United States Patent [19]

Yang

[11] Patent Number: 5,623,029
[45] Date of Patent: Apr. 22, 1997

[54] REINFORCED COMPOSITIONS AND LENS BODIES MADE FROM SAME

[75] Inventor: Shih-Liang S. Yang, Laguna Hills, Calif.

[73] Assignee: Allergan, Waco, Tex.

[21] Appl. No.: 473,393

[22] Filed: Jun. 7, 1995

Related U.S. Application Data

[60] Division of Ser. No. 193,966, Feb. 9, 1994, Pat. No. 5,512,609, which is a continuation-in-part of Ser. No. 48,092, Apr. 15, 1993, abandoned, which is a division of Ser. No. 868,412, Apr. 14, 1992, Pat. No. 5,233,007.

[51] Int. Cl.$^6$ .............................. C08K 5/54; C08G 77/20
[52] U.S. Cl. .............................. 525/478; 528/31; 528/33; 528/43; 525/100; 525/903; 524/731; 523/107
[58] Field of Search .............................. 523/107; 528/31, 528/43, 33; 525/100, 903, 478; 524/731

[56] References Cited

U.S. PATENT DOCUMENTS

| | | | |
|---|---|---|---|
| 2,676,182 | 4/1954 | Daudt et al. | 260/448.2 |
| 2,857,356 | 10/1958 | Goodwin, Jr. | 260/42 |
| 3,088,964 | 5/1963 | Ryan | 528/37 |
| 3,284,406 | 11/1966 | Nelson | 260/465 |
| 3,341,490 | 9/1967 | Burdick | 260/37 |
| 3,457,214 | 7/1969 | Modic | 260/37 |
| 3,479,320 | 11/1969 | Bostick | 528/37 |
| 3,518,324 | 6/1970 | Polmanteer | 525/477 |
| 3,527,659 | 9/1970 | Keil | 117/145 |
| 3,686,254 | 8/1972 | Morehouse | 528/37 |
| 3,992,355 | 11/1976 | Itoh et al. | 106/287 |
| 3,996,187 | 12/1976 | Travnicek | 260/375 |
| 3,996,189 | 12/1976 | Travnicek | 260/375 |
| 4,247,674 | 1/1981 | Koshar et al. | 528/21 |
| 4,380,643 | 4/1983 | Yoshida et al. | 548/260 |
| 4,418,165 | 11/1983 | Polmanteer et al. | 523/210 |
| 4,463,149 | 7/1984 | Ellis | 523/107 |
| 4,500,584 | 2/1985 | Modie | 428/145 |
| 4,535,141 | 8/1985 | Kroupa | 528/15 |
| 4,550,139 | 10/1985 | Arkles | 523/107 |
| 4,573,998 | 3/1986 | Mazzocco | 623/6 |
| 4,615,702 | 10/1986 | Koziol et al. | 623/6 |
| 4,618,665 | 10/1986 | Braun et al. | 528/25 |
| 4,647,282 | 3/1987 | Fedorov et al. | 623/4 |
| 4,737,558 | 4/1988 | Falcetta et al. | 526/279 |
| 4,778,860 | 10/1988 | Morita et al. | 525/431 |
| 4,780,510 | 10/1988 | Uemiya et al. | 526/279 |
| 4,785,047 | 11/1988 | Jensen | 524/714 |
| 4,868,151 | 9/1989 | Reich et al. | 525/479 |
| 4,882,398 | 11/1989 | Mbah | 525/264 |
| 5,006,580 | 4/1991 | Kasuya et al. | 524/264 |
| 5,077,335 | 12/1991 | Schwabe et al. | 524/474 |
| 5,233,007 | 8/1993 | Yang | 528/32 |
| 5,236,970 | 8/1993 | Christ et al. | 528/32 |
| 5,391,590 | 2/1995 | Gerace et al. | 523/107 |

FOREIGN PATENT DOCUMENTS

| | | |
|---|---|---|
| 1273144 | 8/1990 | Canada . |
| 0110537 | 6/1984 | European Pat. Off. . |
| 0202542 | 11/1986 | European Pat. Off. . |
| 0374659 | 9/1989 | European Pat. Off. . |
| 1235722 | 5/1960 | France . |
| 2446818 | 4/1975 | Germany . |
| 3172369 | 7/1991 | Japan . |
| 8000253 | 3/1980 | WIPO . |
| 9321245 | 10/1993 | WIPO . |

OTHER PUBLICATIONS

Gollmar, Preparation of Some Unsaturated Silanes, Journal of Polymer Science Part A1, vol. 9, No. 2, Feb. 1971, pp. 571–574.

Saam, Formation of Linear Siloxane Polymers, 1990 American Chemical Society, pp. 71–89.

Fish et al, Ring Opening Polymerization of Cyclotetrasiloxanes with Large Substituents, pp. 36–37, Polymer Reprints, 31(1), Apr. 1990.

Boutevin et al, Synthesis of Fluorinated Polysiloxanes. 8. Properties at Low and High Temperatures of Polysiloxanes with Fluronated Graft Macromolecules, vol. 24, (3), pp. 629–632(Feb. 4, 1991).

Rasoul et al, Thermal and Rheological Properties of Alkyl–Substitute Polysiloxanes, 1990 American Chemcial Society, pp. 91–96.

Zaph et al, Synthesis and Properties of New UV–Curable Silicones With High Refractive Index, Polymeric Prints 30(2), pp. 107 (1989).

Grigoras et al, Conformational Analysis of Substituted Polysiloxane polymers, 1990 American Chemical Society, pp. 125–144.

Grigoras, Substituted Polysiloxane Polymers:Conformation of the Pendant Groups, Polymer Preprints 31(1), 697(1990).

*Primary Examiner*—Andrew E. C. Merriam
*Attorney, Agent, or Firm*—Frank J. Uxa

[57] ABSTRACT

Compositions, preferably elastomeric compositions, comprise high refractive index polysiloxane-based cross-linked copolymers and high refractive index polymeric resin components. Such compositions, which have refractive indexes of at least about 1.46, preferably at least about 1.48, are useful in producing foldable intraocular lenses.

18 Claims, No Drawings

REINFORCED COMPOSITIONS AND LENS BODIES MADE FROM SAME

RELATED APPLICATIONS

This application is a division of application Ser. No. 08/193,966, filed Feb. 9, 1994, now U.S. Pat. No. 5,512,609 which, in turn, is a continuation-in-part of application Ser. No. 08/048,092, filed Apr. 15, 1993, now abandoned, which, in turn, is a division of application Ser. No. 07/868,412, filed Apr. 14, 1992, now U.S. Pat. No. 5,233,007. The disclosures of each of these applications is incorporated in its entirety herein by reference.

BACKGROUND OF THE INVENTION

The present invention relates to high refractive index, reinforced compositions, and to lens bodies made from such compositions. More particularly, the invention relates to reinforced compositions which have an advantageous combination of properties, including high index of refraction and strength, which are useful in lenses, such as intraocular lenses.

Intraocular lenses (IOLs) have been known for a long time. Such lenses are surgically implanted into the human eye to replace damaged or diseased lenses of the eye.

Whereas IOLs can be made from "hard" polymeric or glass optical materials, soft resilient polymeric materials comprising polysiloxane polymers or copolymers have been increasingly used in the art for this purpose.

IOLs made from silicone polymeric materials are preferably deformable, so that for implantation a smaller incision needs to be surgically cut in the eye than for the implantation of "hard" IOLs. In this respect, the size and mechanical characteristics of the silicone polymeric IOLs play an important role. As it will be well understood by those skilled in the art, for successful implantation the lens must have sufficient structural integrity, strength, elasticity and elongation and small enough size to permit the folding for insertion through a small incision. After insertion, the lens must, of course, regain its original molded shape and have sufficient structural integrity and strength to retain such shape under normal use conditions.

It will be further understood by those skilled in the art that the thinner is the lens, the easier is the surgical insertion procedure. On the other hand, in order to function as an IOL, the lens material must have sufficient optical refractory power. Consequently, the higher is the optical refractive index or index of refraction of the silicone material, the thinner can be the lens to obtain the same optical refractory power.

Some silicone polymeric materials described in the prior art include a reinforcer. Usually such reinforcement of the silicone polymeric material is necessary for the polymeric material to attain adequate structural strength to be used as a foldable IOL. Examples of reinforced silicone polymeric materials suitable for use as soft contact lenses or IOLs are described in U.S. Pat. Nos. 3,996,187 and 3,996,189.

Travnicek U.S. Pat. No. 3,996,189 discloses that the inclusion of diphenyl siloxane or phenyl-methyl siloxane into a polysiloxane increases the refractive index of the composition. This patent discloses silica as a reinforcer or filler component to increase the strength of the composition. Further, this patent discloses that the silicone copolymer has essentially the same refractive index or index of refraction as the silica filler to form a transparent, optically clear contact lens. The silicas useful as strength reinforcers for such elastomers have limited indexes of refraction, being no greater than 1.46. Thus, if it is desired to form an optically clear silicone elastomer-based lens, the elastomer may have to have an index of refraction of 1.46 or less, or may require that no reinforcer component be included. Because of the advantages of high refractive index materials, it would be advantageous to provide an optically clear silicone polymer-based composition with sufficient strength, for example, to be used in lenses and lens bodies.

SUMMARY OF THE INVENTION

New reinforced compositions and lenses, for example, IOLs, made from such reinforced compositions have been discovered. The present compositions can be produced in a relatively easy and straightforward manner. The present optically clear compositions have high refractive indexes, preferably about 1.46 and above, are effectively reinforced to have enhanced strength and structural integrity, and are sufficiently flexible so that IOLs can be produced from such compositions which are foldable so as to be inserted into a human eye through a small surgical incision, for example on the order of about 3 mm.

Compositions, for example, elastomeric compositions, in accordance with the present invention comprise a major amount, that is at least about 50% by weight, preferably about 60% or about 80% to about 99.5% by weight, of a cross-linked copolymer component derived from monomers comprising at least one of polysiloxane and at least one cross-linker component, for example, a polyorganohydrosiloxane; and a polymeric resin component in an amount effective to increase the strength of the composition relative to an identical composition without the polymeric resin component. Such compositions are preferably optically clear. In one embodiment, the cross-linked copolymer component has an index of refraction of at least about 1.46, more preferably at least about 1.48 and still more preferably, at least about 1.50; and the index of refraction of the polymeric resin component is greater than about 1.46, more preferably at least about 1.48 and still more preferably at least about 1.50. The indexes of refraction referred to herein are measured at 25° C.

The index of refraction of the polymeric resin component is preferably within about 0.015 of the index of refraction of the cross-linked copolymer component and more preferably is substantially equal to or matches the index of refraction of the cross-linked copolymer component. The inclusion of polymeric resin components having high indexes of refraction, as described herein, provide effective strength reinforcement for the present compositions and, in addition, allow optically clear compositions to be produced in which the cross-linked copolymer components have very high indexes of refraction. The index of refraction of optically clear silica reinforcers is limited to about 1.46 or less. Thus, prior to the present invention, optically clear reinforced compositions including silica reinforcers were disadvantageously limited as to the index of refraction attainable. The present compositions take full advantage of the high refractive indexes of the cross-linked copolymer component and the polymeric resin component.

Such compositions may be used to produce lens bodies, for example, optics for IOLs, for use in or on a mammalian eye.

DETAILED DESCRIPTION OF THE INVENTION

The present compositions comprise a major amount, preferably about 80% to about 99.5%, by weight of a cross-linked copolymer component derived from (1) at least one polysiloxane and (2) at least one cross-linker component. Such compositions, for example, elastomeric compositions, further comprise a polymeric resin component, which may be covalently bonded to the copolymer component, in an amount effective to increase the strength of the composition relative to an identical composition without the polymeric resin component. The present compositions are preferably silica-free. Preferably the present compositions are optically clear. The present cross-linked copolymer components, and preferably the present compositions, have a refractive index of at least about 1.46, preferably at least about 1.48 and more preferably at least about 1.50. The polymeric resin components have an index of at least about 1.46, preferably refraction of greater than about 1.46, more preferably at least about 1.48 and still more preferably at least about 1.50, and/or have an index of refraction which is within about 0.015 or within about 0.005 of the refractive index of the cross-linked copolymer component. In a particularly useful embodiment, the index of refraction of the polymeric resin component substantially equals or matches the index of refraction of the cross-linked copolymer component. The index of refraction of the polymeric resin component is that of the resin prior to inclusion in the present composition. The index of refraction of the cross-linked copolymer component is that of the cross-linked copolymer without the polymeric resin component.

In one embodiment, the polysiloxane or polysiloxanes have the formula

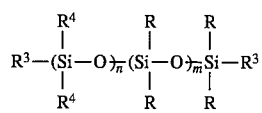

wherein each R and $R^4$ is independently selected from alkyl radicals, aryl radicals, cycloalkyl radicals, aralkyl radicals and substituted counterparts thereof; each $R^3$ is independently selected from monovalent hydrocarbon radicals having a multiple bond and substituted counterparts thereof; n is an integer in the range of about 6 to about 500 or about 1000; and m is an integer in the range of 0 to about 500 or about 1000. Each R is preferably independently selected from alkyl radicals, and each $R^4$ is preferably independently selected from alkyl radicals, aryl radicals and aralkyl radicals. When one $R^4$ is an aryl-containing radical, the other $R^4$ bonded to the same silicon atom is preferably an alkyl radical.

In a particularly useful embodiment, the presently useful polysiloxanes have the formula

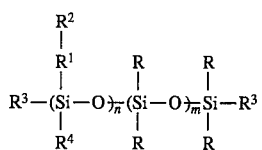

wherein each R and $R^4$ is independently selected as described elsewhere herein; each $R^1$ is independently selected from the group consisting of divalent radicals; each $R^2$ is independently selected from aryl radicals and substituted counterparts thereof; and each $R^3$, n and m are as described elsewhere herein. Each $R^2$ preferably has 6 to about 10 carbon atoms. In one embodiment, $R^2$ is selected from the group consisting of aryl radicals. More preferably, each $R^2$ is phenyl. Preferably, each $R^1$ radical is independently selected from divalent hydrocarbon radicals, more preferably having 1 to about 6 carbon atoms, and substituted counterparts thereof. In one embodiment, each $R^1$ is independently selected from alkylene radicals, more preferably from a methylene radical or an ethylene radical. Without wishing to limit the invention to any particular theory of operation, it is believed that the presence of a spacer group between the aryl group or substituted aryl group and the silicon atom to which it is most directly bonded provides the enhanced flexibility obtained in the present compositions, while, at the same time, having little or no adverse effect on the enhanced refractive index achieved by incorporating such aryl-containing groups in the polysiloxane.

The amount of aryl-containing substituents in the presently useful polysiloxanes is preferably controlled to provide a polysiloxane and/or a cross-linked copolymer component derived from such polysiloxane with the desired refractive index, preferably at least about 1.46, more preferably at least about 1.48 and still more preferably at least about 1.50. The aryl-containing substituents preferably are present in such polysiloxanes in an amount of at least about 10 mol %, more preferably at least about 15 mol % and still more preferably at least about 20 mol %, of the total silicon-bound substituents in such polysiloxane. The aryl-containing substituents may be as much as about 40 mol % or about 50 mol % or more of the total silicon-bound substituents in such polysiloxane. In one embodiment, substantially all of the aryl-containing substituents are the $-R_1-R_2$ groups. In this embodiment, each $R^4$, and more preferably each R and $R^4$, is independently selected from alkyl radicals and substituted alkyl radicals. Still more preferably, each $R_4$ and R is methyl.

Among the alkyl radicals useful in the present polysiloxanes are those which include 1 to about 10 carbon atoms, preferably 1 to about 4 carbon atoms. Examples include methyl, ethyl, propyl, butyl, octyl and decyl. Examples of useful aryl radicals include phenyl, tolyl, xylyl and the like. Examples of useful cycloalkyl radicals include cyclohexyl, cycloheptyl and the like. Examples of useful aralkyl radicals include benzyl, phenylethyl and the like. Each $R^3$ preferably has 2 to about 5 carbon atoms, and more preferably includes 1 carbon—carbon double bond. A particularly useful $R^3$ group is a vinyl group. Substituted counterparts of these radicals may be employed. Thus, such radicals which are substituted with substantially non-interfering substituents that have no substantial or undue detrimental effect on the resulting polysiloxane or on the cross-linked copolymer component or composition produced from such polysiloxane may be employed. Such substituents may include one or more elements, such as oxygen, nitrogen, carbon, hydrogen, halogen, sulfur, phosphorus, and the like and mixtures and combinations thereof.

The present polysiloxanes may be produced by methods which are well known in the art. Many of such polysiloxanes are commercially available. Therefore, methods for producing such polysiloxanes are not described in detail herein. One useful method of producing polysiloxanes, particularly polysiloxanes including $-R^1-R^2$ groups, as described herein is as follows:

Such method comprises:

(a) contacting a cyclic hydride-containing siloxane monomer with at least one component having the formula $R^2$-f wherein $R^2$ is as described previously, and f is a functional monovalent radical capable of reacting with a silicon bonded hydride group of the cyclic hydride-containing siloxane monomer at conditions effective to chemically react the component with at least one of these hydride groups and form a cyclic aryl-containing siloxane monomer containing at least one -R¹-R² group wherein R¹ and R² are as described previously; and (b) contacting the cyclic aryl-containing siloxane monomer with at least one siloxane monomer at conditions effective to decyclize and polymerize the cyclic aryl-containing siloxane monomer, polymerize the siloxane monomer and form a polysiloxane having the following units

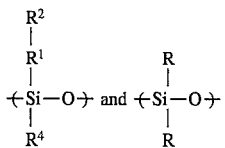

wherein each R and R⁴ is independently selected as described above.

In another embodiment, methods for making polysiloxanes provide for a step (b) which comprises contacting the cyclic aryl-containing siloxane monomer at conditions effective to decyclize and polymerize the cyclic aryl-containing siloxane monomer and form a polysiloxane having a repeating unit of

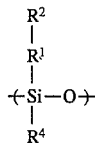

wherein each R⁴ is independently selected as described above.

In many instances, at least one precursor of end blocking groups is included in step (b) and is reacted together with the other monomer or monomers present to form the end or terminal groups of the polysiloxanes. Such precursors, for example, disiloxanes, are such to provide the R³ groups to the present polysiloxanes. These precursors preferably include two terminal or end silicon atoms and an R³ group bonded to each of the terminal silicon atoms. The precursor or precursors of end blocking groups are preferably included in step (b) in an amount effective to provide the polysiloxane formed with end blocking groups, such as described herein.

In step (a) of the above-noted methods, cyclic hydride-containing siloxane monomers are employed. Such monomers include three or more, preferably 3 to about 6, silicon atoms in a cyclic structure. Such monomers include at least one silicon bonded hydride group, i.e., Si—H. Preferably, two or more such hydride groups are included in the cyclic hydride-containing monomers. In a particular useful embodiment, each of the silicon atoms of such cyclic monomers has at least one, and more preferably only one, hydride group directly bonded thereto. A number of useful cyclic hydride-containing siloxane monomers are commercially available. One especially useful such monomer is tetrahydrotetramethylcyclotetrasiloxane.

Step (a) of the present methods may comprise contacting the cyclic hydride-containing siloxane monomer or monomers with at least one component having a formula R²-f where f includes a carbon—carbon multiple, preferably double, bond at effective hydrosilation conditions.

The contacting at hydrosilation conditions may be catalyzed using, for example, one or more platinum group metal components, many of which are commercially available and conventionally used in vinyl/hydride addition curing of silicone polymers. The amount of platinum group metal, preferably platinum, component employed is effective to promote the desired hydrosilation in step (a). Such amount may be within the range of about 0.01 part per million (ppm) to about 100 ppm (or more) by weight of the total reactants present in step (a), calculated as elemental platinum group metal.

Step (a) may be conducted at hydrosilation conditions effective to provide the desired product. For example, temperatures in the range of about 10° C. or lower to about 60° C. or higher may be employed. Contacting times in the range of about 10 minutes to about 10 hours or longer have been found to be useful. Since the desired hydrosilation reaction of step (a) is often exothermic, the temperature of the reaction mixture may advantageously be controlled, e.g., by a cooling medium, to maintain the temperature in the desired range.

Alternately, step (a) can be accomplished using a Grignard-type reaction. In such a reaction, each component R²-f is in the form of a so called Grignard reagent, the preparation of which is well known in the art. In this embodiment, step (a) may comprise contacting the cyclic hydride-containing siloxane monomer with a component such a Grignard reagent at effective Grignard reaction conditions to produce the desired cyclic aryl-containing siloxane monomer. Such Grignard reaction conditions include, for example, reaction temperatures in the range of about −60° C. or lower to about 0° C. or higher; and reaction times in the range of about 10 minutes to about 10 hours or longer.

The cyclic aryl-containing siloxane monomers alone or with other siloxane monomers, and preferably with precursors of end blocking groups, are reacted in the presence of a suitable catalyst to achieve decyclization and polymerization to the desired degree. The reactions can be conducted by using one or more of a variety of catalysts. Many such catalysts are well known in the art of cyclic siloxane polymerization. Examples of such catalysts include potassium hydroxide, tetramethyl ammonium hydroxide, derivatives thereof and mixtures thereof.

The amount of catalyst used in and the conditions at which step (b) occurs may be similar to those parameters which are conventionally employed in decyclizing and polymerizing other cyclic siloxane monomers. For example, the amount of catalyst employed may be in the range of about 0.01% to about 1% by weight of the total reactants. Temperatures in the range of about 20° C. to about 150° C. and reaction times in the range of about 0.5 hours to about 6 hours or more may be employed.

The degree of polymerization in step (b) is preferably monitored by monitoring the viscosity of the reaction mixture.

After the desired level or degree of polymerization is achieved, the catalyst is inactivated, neutralized, or removed, and the reaction product may be filtered.

After filtration, volatile materials are removed from the polysiloxane, for example, by repeated vacuum stripping.

Particularly useful cross-linker components are selected from polyorganohydrosiloxanes and mixtures thereof. Many such polyorganohydrosiloxanes are commercially available and/or well known in the art for providing vinyl/hydride addition cure silicone polymers. In order to obtain enhanced compatibility between the polysiloxane and the cross-linker component and/or enhanced refractive index of the cross-linked copolymer component, it is preferred that the cross-linker component have a refractive index which is substantially the same, for example, within about 0.05 and preferably within about 0.02, as the refractive index of the polysiloxane. Examples of particularly useful cross-linker components include copolymers of methylhydrosiloxane and phenylmethylsiloxane, copolymers of methylhydrosiloxane and diphenylsiloxane, and mixtures thereof.

The elastomeric compositions of the present invention include a polymeric resin component in an amount effective to increase the strength of the composition relative to an identical composition without the polymeric resin component.

In accordance with one embodiment of the invention, the polymeric resin component is preferably used in a ratio of about 0.5 to about 20 parts by weight of the polymeric resin component to 100 parts of the total composition. A number of organic resins (that is silicon-based resins including organic groups) are known to be useful for reinforcing articles which include silicone elastomers. Of course, the reinforcer component used in the present compositions employed in optical applications should be optically clear or at least have no significant detrimental effect on the optical clarity of the compositions. In one embodiment, the refractive index of the polymeric resin component is preferably at least about equal to or greater than the refractive index of the cross-linked copolymer component of the present compositions.

Examples of useful polymeric resin components include: the polymeric form of the cohydrolyzate of a trialkyl hydrolyzable silane and an alkyl silicate as described in Goodwin, Jr. U.S. Pat. No. 2,857,356; resins formed by reacting silanes or siloxanes with a silica hydrosol as described in Daudt U.S. Pat. No. 2,676,182; and resinous organopolysiloxane copolymers as described in Modic U.S. Pat. No. 4,500,584. The disclosure of each of the patents referred to in this paragraph is incorporated in its entirety herein by reference.

A particularly useful class of polymeric resin components are resinous organopolysiloxane copolymers which comprise $(R^c)_3 SiO_{0.5}$ and $SiO_2$ units and resinous organopolysiloxane copolymers which comprise $(R^d)_3SiO_{0.5}$, $(R^d)_2SiO$ and $SiO_2$ units and mixtures of such resinous copolymers, for example, as described in the above-noted Modic Patent. The $R^c$ group and $R^d$ groups are selected from vinyl radicals and monovalent hydrocarbon radicals free of aliphatic unsaturation. Particularly useful materials are those in which about 1.5 mol % to about 10 mol % of the silicon atoms included contain silicon-bonded vinyl groups. Such vinyl groups are very effective in reacting to covalently bond the polymeric resin component to the cross-linked copolymer component of the present compositions. Each of the $R^c$ groups which are not vinyl are preferably independently selected from alkyl radicals, aryl radicals, cycloalkyl radicals, aralkyl radicals and substituted counterparts thereof, and more preferably are aralkyl, such as benzyl, radicals. The ratio of $(R^c)_3 SiO_{0.5}$ units to $SiO_2$ units in the resinous copolymer is preferably in the range of about 0.5 to about 1. The ratio of $(R^d)_3SiO_{0.5}$ units to $SiO_2$ units is preferably in the range of about 0.5 to about 1, and, more preferably, the ratio of difunctional units, $(R^d)_2SiO$ units, to tetrafunctional units, $SiO_2$ units, ranges up to about 0.1.

The organopolysiloxane resinous copolymers described above are known in the art as MQ resins. Methods for producing such resins are well known in the art and are not described in detail here. Care should be taken in selecting the specific resin for use to insure it meets the requirements of the application involved. For example, the resin employed should provide a polymeric resin component which is an effective reinforcing component and has the desired index of refraction. In addition, if the final composition is to be optically clear, the resin should be chosen so as to have no undue detrimental effect on such optical clarity.

In the preparation of the present elastomeric compositions, the polysiloxane is preferably intimately mixed with the polymeric resin component. The intimate mixing is preferably aided by treating the mixture on a roll mill or like device. After intimate mixing, additional volatiles may be removed from the mixture by heat and vacuum.

This intimate mixture of polysiloxane and polymeric resin component is hereinafter referred to as the "base". For the purpose of making materials suitable for use in IOLs, the base may be dispersed in a suitable inert solvent, such as trichlorotrifluoroethane (FREON), and the dispersion filtered to remove any solid impurities. Thereafter, the solvent is removed by gentle heat and vacuum.

The base preferably has the inherent characteristic of providing, after suitable curing by cross-linking, an elastomeric composition having physical properties which are highly advantageous for inclusion in a foldable IOL. Thus, after the curing or cross-linking step, the properties of the resulting cross-linked elastomeric composition preferably include in accordance with the present invention the following:

an optical refractive index which is at least about 1.46, more preferably at least about 1.48 and still more preferably at least about 1.50;

a Shore A durometer hardness value of at least about 25;

a tensile strength of at least about 300 psi or about 400 psi;

a tear strength of at least about 20 pounds per lineal inch (pli); and an elongation of at about 100%, preferably at least about 200%.

The above listed properties can be measured in accordance with state-of-the-art technology and instruments in accordance with the respective requirements of standard ASTM test methods. More particularly, the durometer test is performed as ASTM D2240, the tensile and elongation tests as ASTM D412 and the tear strength test as ASTM D624 Die B.

In one embodiment, the durometer hardness is about 30 or about 38 to about 40, the tensile strength is in the range of about 300 or about 700 to about 750 psi, and the tear strength is about 20 psi to about 40 pli. In this regard it is noted that cross-linking tends to slightly increase the optical refractive index as compared to the uncured base.

Preparation of the uncured base for cross-linking is preferably accomplished as follows. The base is divided into two aliquots which preferably are of equal weight. The aliquots are termed "Part A" and "Part B" or first and second aliquot parts. Cross-linking may be accomplished by utilizing a platinum group metal catalyzed reaction of the terminal silicon bonded multiple bonds (vinyl groups) of the base, and silicon bonded hydrogens or hydride groups of the cross-linking agent. The silicon bonded multiple bonds (vinyl groups) are present in both the first and second aliquots of the base.

Silicon bonded hydrogens or hydride groups are added in the practice of the present invention to the second aliquot (Part B) in the form of one or more suitable cross-linking agents, such as a polyorganohydrogen siloxane. The cross-linking agents per se are known in the art, and may be made in accordance with the teachings of U.S. Pat. No. 3,436,366, which is incorporated in its entirety herein by reference.

The platinum group metal, preferably platinum, catalyst can be selected from such catalysts which are conventional and well known in the art. Suitable catalysts include organo platinum group metal, preferably platinum, compounds, for example, in accordance with U.S. Pat. Nos. 2,823,218 and 3,159,601, each of which is incorporated in its entirety herein by reference. The catalyst may be added to the first aliquot (Part A).

After mixing of the aliquots (Part A and Part B), the cross-linking preferably should not proceed too rapidly at room temperature, thereby allowing at least about 2, more preferably at least about 4 or about 6, hours for work time with the mixed aliquots. For this reason, a suitable cross-linking inhibitor, such as 1, 2, 3, 4 tetramethyl-1,2,3,4-tetravinyl cyclotetrasiloxane, is preferably added to the second aliquot (Part B).

The platinum group metal catalyst is present in the first aliquot in an amount in the range of about 1 ppm to about 50 ppm by weight. The cross-linker is preferably included in the second aliquot in an amount in the range of about 0.5 or about 1 to about 6 or about 10 parts per hundred by weight. The cross-linking inhibitor is preferably added to the second aliquot in an amount in the range of about 0.01 to about 0.2 parts per hundred by weight.

An ultraviolet light absorbing material, preferably a polymerizable ultraviolet light absorbing material, may be mixed into the second aliquot.

The ultraviolet light absorbing material, for example, selected from vinyl functional 2-hydroxybenzophenones and vinyl functional benzotrizoles, is preferably covalently linked to the silicone elastomer of the elastomeric composition during the cross-linking step. The ultraviolet light absorbing material is preferably added to the second aliquot in an amount in the range of about 0.1% to about 1% or about 5% by weight. The curing or cross-linking occurs at conditions effective to provide the desired elastomeric composition. Curing temperatures may vary, for example, from about 20° C. to about 200° C., and curing times may range, for example, from about 1 minute to about 5 hours or about 10 hours or more.

Formation of IOL bodies or optics from the elastomeric compositions of the present invention may be accomplished by liquid injection molding or by cast or compression molding or other types of molding of the intimately mixed first and second aliquots. These processes are well known in the art.

The following non-limiting examples illustrate certain aspects of the present invention.

EXAMPLE 1

24 g of tetramethylhydrocyclotetrasiloxane (from Petrarch System, Inc.) is added dropwise into a 25 g toluene solution containing 25 g styrene (Aldrich Chemical Company) and 1 ml platinum complex solution (Petrarch System, Inc.). The reaction is exothermal and is controlled at 40° C. using an ice bath. After complete addition of the tetramethylhydrocyclotetrasiloxane in 30 minutes, the reaction temperature is slowly raised from 40° to 75° C. in one hour and is maintained at 75° C. for another hour. The toluene solvent and unreacted styrene is removed by vacuum distillation. After the volatiles are removed, the product flask is found to contain 34 g of tetramethylstyrlcyclotetrasiloxane.

'H-NMR analysis indicates that alpha and beta substitutions have a ratio of about 1 to 1.6 and are as shown in the chemical structure illustrated below. The tetramethylstyrlcyclotetrasiloxane monomer has a refractive index of 1.53.

The above described reaction is illustrated as follows:

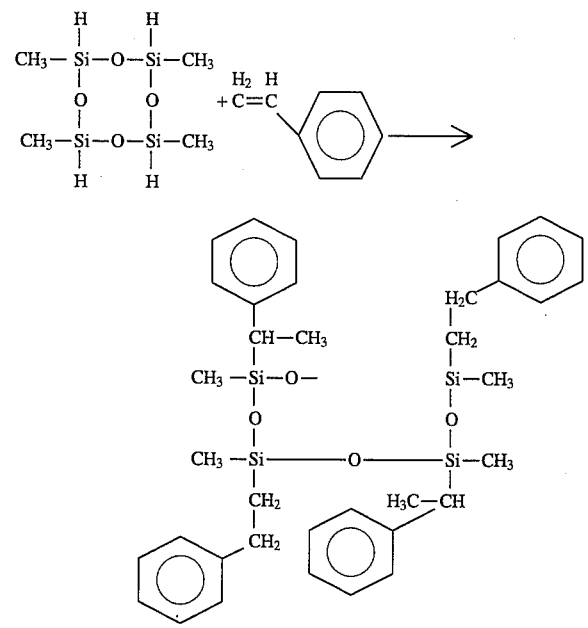

EXAMPLE 2

In a 2 liter reactor, tetramethylstyrylcyclotetrasiloxane (1088 g) and 1, 2 divinyltetramethyldisiloxane (6 g) are mixed and heated with agitation under a nitrogen gas blanket to 100° C. When the temperature reaches 100° C., 0.18 percent (by weight) N-catalyst (tetramethyl ammonia hydroxide) is added. Stirring and heating are continued and the viscosity of samples taken from the reaction mixture is monitored. If after 45 minutes there is no change in viscosity, an additional 0.09 percent N-catalyst is added. After heating and stirring for another 3 hours, the catalyst is destroyed by heating the mixture to 150° C. The viscosity of the cooled reaction mixture should be between 2000 and 2800 cp. The refractive index should be between 1.52 and 1.54.

The polymer is stripped three times on a wipe film evaporator. The viscosity of the stripped polymer should be between 4100 and 5300 cp, and the refractive index should be between 1.53 and 1.54. This polymer is a vinyl terminated methyl-styrylpolysiloxane.

EXAMPLE 3

The stripped polymer from Example 2 is passed through a 325 mesh steel wire screen under pressure. A MQ resin having an index of refraction of 1.53 is added to this stripped polymer so that the resin is equal to 10% by weight of the total batch. The batch is divided into two equal parts, Part A and Part B. 12 parts per million by weight of the organo-platinum catalyst identified in Example 1 is mixed into Part A. Small samples from Part B are mixed with various concentrations of a cross-linker, a liquid organohydrogen polysiloxane having a refractive index of 1.50 and sold by Petrarch Systems under the trademark PS 129.5. The cross-linker level is optimized so as to obtain a Shore durometer hardness of approximately 25 or higher (ASTM D2240) in the cross-linked product. Thereafter, increasing amounts of an inhibitor (1,2,3,4 tetramethyl-1,2,3,4-tetravinyl cyclotetrasiloxane) are added to Part B and mixed samples of parts A and B are tested to obtain a working time of about 6 hours or longer at room temperature. Depending on the above-noted sample test results, the cross-linker is added to Part B to provide 1–6 parts per hundred by weight, and the inhibitor is added to part B to provide 0.01 to 0.2 parts per hundred by weight.

An effectively reinforced elastomeric composition prepared by curing equal amounts of Parts A and B (with 6 parts per hundred by weight of cross-linker at 100° C. for 30 minutes) has a refractive index of about 1.53 and sufficient tensile strength, elongation and tear strength to be useful for making foldable IOLs.

While this invention has been described with respect to various specific examples and embodiments, it is to be understood that the invention is not limited thereto and that it can be variously practiced within the scope of the following claims.

What is claimed is:

1. A composition comprising:

a major amount by weight of a cross-linked copolymer component derived from monomers comprising (1) at least one polysiloxane including aryl-containing substituents and (2) at least one cross-linker component selected from the group consisting of polyorganohydrosiloxanes and mixtures thereof; and a polymeric resin component selected from the group consisting of silicon-based resins including organic groups and mixtures thereof in an amount effective to increase the tensile strength of said composition relative to an identical composition without said polymeric resin component, said composition being optically clear, said cross-linked copolymer component and said polymeric resin component each having an index of refraction of at least about 1.46, said composition being elastomeric.

2. The composition of claim 1 wherein the index of refraction of said polymeric resin component is within about 0.015 of the index of refraction of said cross-linked copolymer component.

3. The composition of claim 1 wherein the index of refraction of said polymeric resin component is greater than 1.46 and is substantially equal to the index of refraction of said cross-linked copolymer component.

4. The composition of claim 1 wherein the index of refraction of each of said cross-linked polymer component and said polymeric resin component is at least about 1.48.

5. The composition of claim 1 wherein the index of refraction of each of said cross-linked polymer component and said polymeric resin component is at least about 1.50.

6. The composition of claim 1 wherein said polymeric resin component is a material selected from the group consisting of resinous organopolysiloxane copolymers which comprise $(R^c)_3 SiO_{0.5}$ units and $SiO_2$ units, resinous organopolysiloxane copolymers which comprise $(R^d)_3SiO_{0.5}$ units, $(R^d)_2SiO$ units, and $SiO_2$ units and mixtures thereof, wherein $R^c$ and $R^d$ are independently selected from the group consisting of vinyl radicals and monovalent hydrocarbon radicals free of aliphatic unsaturation.

7. The composition of claim 6 wherein about 1.5 mol % to about 10 mol % of the silicon atoms included in said material contain silicon-bonded vinyl groups.

8. The composition of claim 6 wherein each of the $R^c$ groups and $R^d$ groups which is not vinyl is independently selected from the group consisting of alkyl radicals, aryl radicals, cycloalkyl radicals, aralkyl radicals and substituted counterparts thereof.

9. The composition of claim 6 wherein at least a portion of the $R^c$ groups and the $R^d$ groups which are not vinyl are benzyl radicals.

10. The composition of claim 1 wherein said at least one polysiloxane has the formula

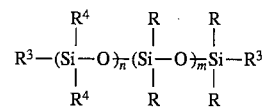

wherein each R and $R^4$ is independently selected from the group consisting of alkyl radicals, aryl radicals, cycloalkyl radicals, aralkyl radicals and substituted counterparts thereof; each $R^3$ is independently selected from the group consisting of monovalent hydrocarbon radicals having a multiple bond and substituted counterparts thereof; n is an integer in the range of about 6 to about 500; and m is an integer in the range of 0 to about 500.

11. The composition of claim 10 wherein each R is independently selected from the group consisting of alkyl radicals and each $R^4$ is independently selected from the group consisting of alkyl radicals, aryl radicals and aralkyl radicals.

12. The composition of claim 11 wherein when one $R^4$ is an aryl-containing radical, the other $R^4$ bonded to the same silicon atom is an alkyl radical.

13. A composition comprising:

a major amount by weight of a cross-linked copolymer component derived from monomers comprising (1) at least one polysiloxane including aryl-containing substituents and (2) at least one cross-linker component selected from the group consisting of polyorganohydrosiloxanes and mixtures thereof; and a polymeric resin component selected from the group consisting of silicon-based resins including organic groups and mixtures thereof in an amount effective to increase the tensile strength of said composition relative to an identical composition without said polymeric resin component, said cross-linked copolymer component having an index of refraction of at least about 1.46, the index of refraction of said polymeric resin component being within about 0.015 of the index of refraction of said cross-linked copolymer component, and said composition being elastomeric and optically clear.

14. The composition of claim 13 wherein said cross-linked copolymer component has an index of refraction of at least about 1.48.

15. The composition of claim 13 wherein said cross-linked copolymer component has an index of refraction of at least about 1.50.

16. The composition of claim 13 wherein said polymeric resin component comprises $(R^c)_3 SiO_{0.5}$ units and $SiO_2$ units, wherein $R^c$ is selected from the group consisting of vinyl radicals and monovalent hydrocarbon radicals free of aliphatic unsaturation.

17. The composition of claim 1 which is silica-free.

18. The composition of claim 13 which is silica-free.

* * * * *